United States Patent
Fournier et al.

(10) Patent No.: US 9,839,752 B2
(45) Date of Patent: Dec. 12, 2017

(54) NEEDLE PROTECTION DEVICE

(71) Applicant: APTAR STELMI SAS, Villepinte (FR)

(72) Inventors: Arnaud Fournier, Paris (FR); Ghislain Fournier, La Rochelle (FR); Mickael Swal, Chauconin Neufmontiers (FR)

(73) Assignee: APTAR STELMI SAS, Villepinte (FR)

( * ) Notice: Subject to any disclaimer, the term of this patent is extended or adjusted under 35 U.S.C. 154(b) by 0 days.

(21) Appl. No.: 14/760,849

(22) PCT Filed: Feb. 25, 2014

(86) PCT No.: PCT/FR2014/050395
§ 371 (c)(1),
(2) Date: Jul. 14, 2015

(87) PCT Pub. No.: WO2014/131981
PCT Pub. Date: Sep. 4, 2014

(65) Prior Publication Data
US 2015/0352291 A1 Dec. 10, 2015

(30) Foreign Application Priority Data
Mar. 1, 2013 (FR) ..................................... 13 51849

(51) Int. Cl.
*A61M 5/32* (2006.01)
*A61M 5/31* (2006.01)
*A61M 5/34* (2006.01)

(52) U.S. Cl.
CPC ........ *A61M 5/3204* (2013.01); *A61M 5/3202* (2013.01); *A61M 5/3216* (2013.01);
(Continued)

(58) Field of Classification Search
CPC .............. A61M 5/3202; A61M 5/3216; A61M 2005/3109; A61M 2005/312;
(Continued)

(56) References Cited

U.S. PATENT DOCUMENTS

| | | | | |
|---|---|---|---|---|
| 791,802 A | * | 6/1905 | De Lisle | A61M 5/28 604/193 |
| 3,073,307 A | * | 1/1963 | Stevens | A61M 5/002 206/365 |

(Continued)

FOREIGN PATENT DOCUMENTS

| | | |
|---|---|---|
| EP | 1 208 861 A1 | 5/2002 |
| FR | 2 777 787 A1 | 10/1999 |

(Continued)

OTHER PUBLICATIONS

International Search Report for PCT/FR2014/050395 dated Jul. 3, 2014 [PCT/ISA/210].

(Continued)

*Primary Examiner* — Kevin C Sirmons
*Assistant Examiner* — William Carpenter
(74) *Attorney, Agent, or Firm* — Sughrue Mion, PLLC (57) ABSTRACT

A fluid injection device having a syringe body, a needle, and a needle protection device removable from the injection device and having a substantially flexible or deformable inner body and a substantially rigid outer body. In the stored position the inner body closes the dispenser orifice of the needle and the outer body co-operates with the injection device to fasten the protection device on the injection device. The protection device includes a protection system against accidental pricking, having protective flaps that are integral part of the outer body and movable between a covering position in which they cover the needle, and an open position in which the needle is uncovered. The protection system has a control ring that slides over the outer body so as to move the flaps from their covering position to their open position, before injection, and from their open position to their covering position, after injection.

14 Claims, 7 Drawing Sheets

(52) U.S. Cl.
CPC ....... *A61M 5/343* (2013.01); *A61M 2005/312* (2013.01); *A61M 2005/3107* (2013.01)

(58) Field of Classification Search
CPC ........ A61M 2005/3118; A61M 5/3213; A61M 2005/3107; A61M 5/3204; A61M 5/343
See application file for complete search history.

(56) References Cited

U.S. PATENT DOCUMENTS

| | | | |
|---|---|---|---|
| 4,829,277 A | 5/1989 | Stahura et al. | |
| 4,950,249 A * | 8/1990 | Jagger | A61M 5/3216 604/192 |
| 4,966,591 A | 10/1990 | Yuen | |
| 4,986,818 A * | 1/1991 | Imbert | A61M 5/3213 604/192 |
| 6,156,012 A | 12/2000 | Nathan | |
| 6,186,980 B1 * | 2/2001 | Brunel | A61M 5/3202 604/110 |
| 6,413,243 B1 * | 7/2002 | Geist | A61M 5/3216 604/110 |
| 6,503,230 B2 * | 1/2003 | Odell | A61M 5/3202 604/192 |
| 6,551,286 B1 * | 4/2003 | Claessens | A61M 5/3202 128/919 |
| 7,112,190 B2 * | 9/2006 | Bressler | A61M 25/0637 604/263 |
| 8,002,756 B2 * | 8/2011 | Walters | A61M 39/0208 604/192 |
| 8,512,295 B2 * | 8/2013 | Evans | A61M 5/3202 215/216 |
| 2002/0062108 A1 * | 5/2002 | Courteix | A61M 5/3202 604/198 |
| 2009/0171311 A1 | 7/2009 | Genosar et al. | |
| 2016/0015905 A1 * | 1/2016 | Fournier | A61M 5/3202 604/192 |

FOREIGN PATENT DOCUMENTS

| | | |
|---|---|---|
| FR | 2 803 530 A1 | 7/2001 |
| WO | 2012/012601 A1 | 1/2011 |

OTHER PUBLICATIONS

International Preliminary Report on Patentability dated Sep. 3, 2015 issued by the International Bureau in counterpart International Application No. PCT/FR2014/050395.

* cited by examiner

NEEDLE PROTECTION DEVICE

CROSS REFERENCE TO RELATED APPLICATIONS

This application is a National Stage of International Application No. PCT/FR2014/050395, filed on Feb. 25, 2014, which claims priority from French Patent Application No. 13 51849, filed on Mar. 1, 2013, the contents of all of which are incorporated herein by reference in their entirety.

The present invention relates to an injection device including a needle protection device.

Needle protection devices, also known as needle guards, are well known. Various types exist, including rigid needle guards that have an inner body made of flexible material and an outer body made of rigid material. The inner body guarantees sealing both of the orifice of the needle and of the injection device, generally the syringe body, while the outer body serves to fasten and maintain the needle guard on the injection device until said device is used. Documents EP 1 208 861 and FR 2 777 787 describe in particular needle protection devices of that type. Documents US 2009/171311, WO 2012/012601, U.S. Pat. No. 4,966,591, FR 2 803 530, U.S. Pat. No. 4,829,277, and U.S. Pat. No. 6,156,012 describe other prior-art devices.

Those devices may present certain drawbacks. Thus, it is not possible to prevent the needle guard from being removed inadvertently or accidentally prior to using its associated injection device, which could result in a risk of contamination of the needle. In addition, in particular as a result of manufacturing tolerances, in particular of syringes made of glass, in some circumstances it may be difficult, in the stored position, to guarantee sealing between the deformable inner body of the needle guard and the injection device, specifically the syringe body made of glass. In addition, manufacturing and assembling the needle guard, and in particular assembling the outer body on the inner body, may be complex and thus costly. In addition, even if the needle guard is effective in its stored position, it does not make it possible to prevent or avoid any risk of injury from the needle after using the injection device.

An object of the present invention is to provide an injection device including a needle protection device that does not have the above-mentioned drawbacks.

An object of the present invention is thus to provide such a needle protection device that guarantees sealing prior to use.

Another object of the present invention is to provide such a needle protection device that indicates to the user if the seal has been broken prior to use.

Another object of the present invention is to provide such a needle protection device that is simple and easy to manufacture and to assemble, and that is reliable in its use.

The present invention thus provides a fluid injection device comprising a syringe body and a needle that is fastened in an axial end projection of the syringe body, said injection device further comprising a needle protection device, said protection device being fastened on said injection device in a stored position, said protection device being removable from said injection device, said protection device comprising an inner body that is made of material that is substantially flexible or deformable, and an outer body that is made of material that is substantially rigid, in the stored position said inner body closing the dispenser orifice of said needle in leaktight manner, and co-operating with said injection device in leaktight manner, and in the stored position said outer body co-operating with said injection device so as to fasten said protection device on said injection device, said needle protection device including a protection system for protecting against accidental pricking, said protection system comprising protective flaps that form an integral part of said outer body, said protective flaps being movable between a covering position in which they cover the needle, and an open position in which the needle is uncovered, said protection system further comprising a control ring that slides over said outer body so as to move said protective flaps from their covering position to their open position, before injection, and from their open position to their covering position, after injection.

Advantageously, said inner body includes a radial projection, and said outer body includes a radial shoulder and a radial end edge that defines a top axial opening, said inner body being inserted in said outer body through said top axial opening, with said radial projection in abutment against said radial shoulder, said axial end edge of said outer body being folded down on said inner body so as to fasten said inner body in said outer body.

Advantageously, said axial end edge of said outer body is folded down on said inner body after assembling said needle protection device on said injection device.

Preferably, said axial end edge of said outer body is folded down on said inner body prior to assembling said needle protection device on said injection device.

Advantageously, said axial end projection is defined between an axial end surface of the syringe body and a radial projection, said outer body including a fastener portion that is fastened, in particular snap-fastened, on said axial end projection.

Advantageously, said outer body includes a protective portion that is fastened to said inner body, said protective portion is connected to said fastener portion via at least one breakable bridge of material, said at least one breakable bridge of material being broken so as to remove said protective portion and said inner body from said injection device.

Advantageously, the force required to remove said fastener portion from said injection device is greater than the force required to break said at least one breakable bridge of material.

Advantageously, said control ring includes at least one axial end edge portion that co-operates with said protective flaps so as to move them from their covering position to their open position.

Advantageously, said protective flaps are pivotable and are connected to said outer body via flexible hinges.

Advantageously, each of said protective flaps includes at least one axial tab, having an end that is preferably rounded, that co-operates with said at least one axial end edge portion of the control ring.

Advantageously, in their covering position, said protective flaps define at least one slot that is adapted to receive said at least one axial end edge portion of the control ring.

Advantageously, said outer body and/or said control ring include blocking means for holding said control ring on said outer body in a first position, with the protective flaps in their open position, and in a second position, with the protective flaps in their covering position.

Advantageously, said blocking means are formed by at least one rib that is formed on one of the outer body and the control ring, and that co-operates with at least one groove that is formed on the other one of the outer body and the control ring.

Advantageously, said inner body is made of rubber.

These characteristics and advantages and others of the present invention appear more clearly from the following detailed description, given by way of non-limiting example, and with reference to the accompanying drawing, and in which.

The present invention is described with reference to several variant embodiments of a needle protection device for an injection device. However, naturally the present invention is not limited by the embodiments shown in the drawings.

Figure 1:
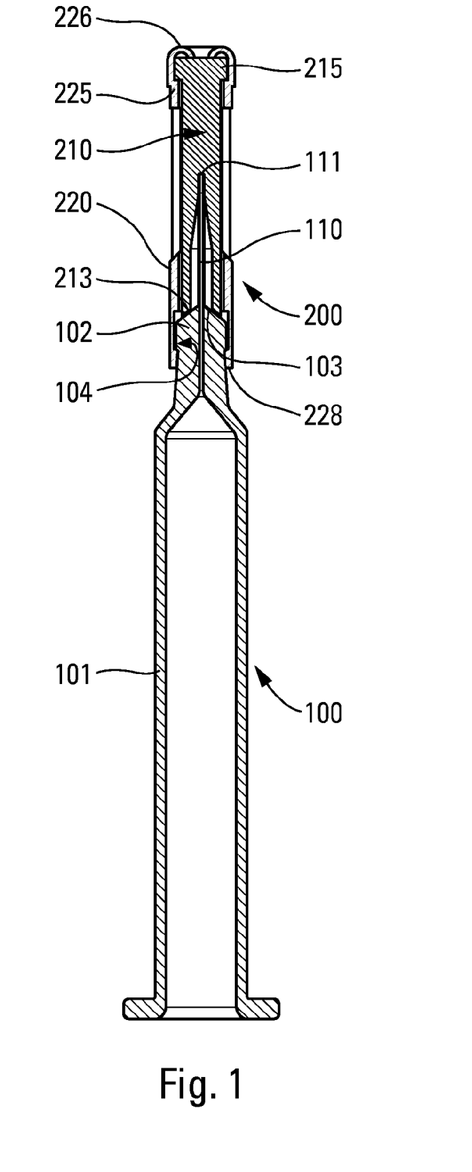
FIGS. 1 and 2 are diagrammatic section views of a needle protection device in a first advantageous variant embodiment, respectively in its stored position on an injection device and in its removed position.
Figure 2:
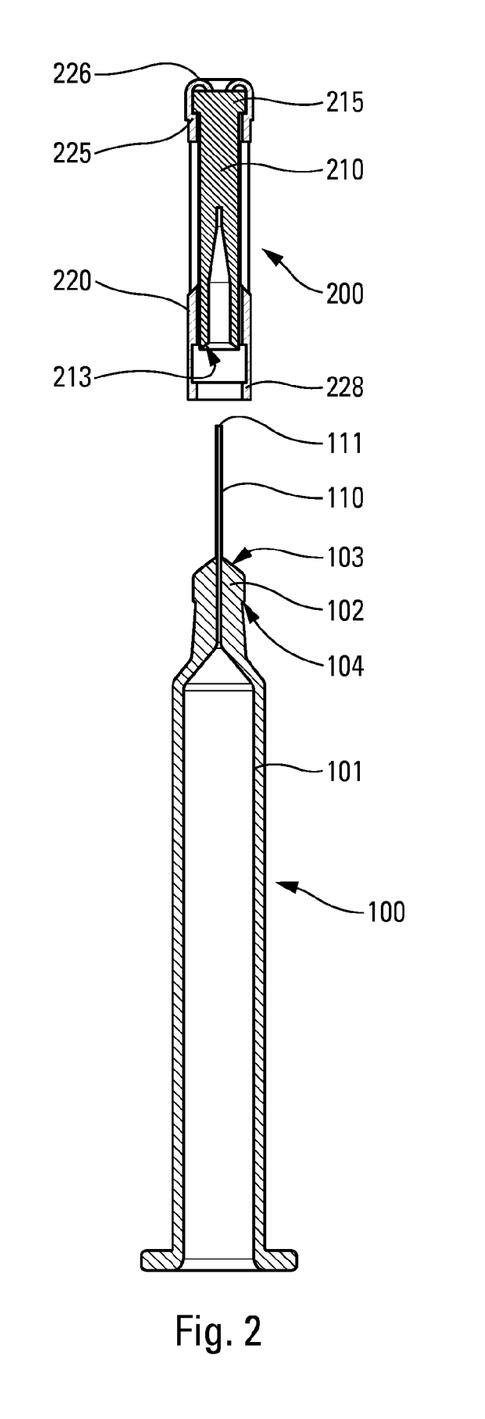

With reference to FIGS. 1 and 2, an injection device is shown that, in this embodiment, is a syringe 100 that is provided with a syringe body 101 and with a needle 110 that includes a dispenser orifice 111. The axial end portion of the syringe body that fastens the needle 110 includes an axial end projection 102, generally known as the hub of the syringe, that is defined between the axial end surface 103 of the syringe body, and a radial projection 104 that is for receiving and fastening a needle protection device 200 that is described below. The needle typically has a length of 12.7 millimeters (mm) (½ inch ("")), 15.9 mm (⅝"), or 25.4 mm (1"). Other sizes may also be envisaged.

A needle protection device 200 is provided so as to protect said needle and keep it leaktight until the injection device is used. The needle protection device 200 is fastened on said injection device 100 in its stored position, and it is removable, i.e. it may be removed from said injection device when said injection device is to be used. The needle protection device 200 comprises an inner body 210 and an outer body 220.

The inner body 210 is made of material that is substantially flexible or deformable, such as polyisoprene, styrene-butadiene rubber (SBR), a thermoplastic elastomer (TPE), or any other elastomer, for example. Other materials may also be envisaged. The inner body 210 includes a solid portion that, in the stored position of the needle protection device, receives the dispenser orifice 111 of the needle 110. The axial end of the needle 110 is thus embedded in said inner body 210 in said stored position. The inner body 210 also includes a radial projection 215 that is formed at the distal axial end of said inner body relative to said injection device. On the other side, at the other axial end, the inner body 210 forms a hollow sleeve, and includes an axial end edge 213 that is proximal relative to the injection device, having a shape that is complementary to the axial end surface 103 of the hub 102 of the syringe.

The outer body 220 is preferably made as a single piece out of a material that is substantially rigid, such as polypropylene (PP), polystyrene (PS), polyoxymethylene (POM), or polybutyl terephthalate (PBT), for example. Other materials may also be envisaged. The outer body 220 includes a fastener portion 228 that is adapted to co-operate with the syringe body 101, in particular with the hub 102 of the syringe, and more particularly with the radial shoulder 104, so as to fasten, in particular by snap-fastening, said needle protection device 200 on said injection device 100. At the other end, namely the distal end relative to the injection device, the outer body 220 includes a radial shoulder 225 and an axial end edge 226 that defines a top axial opening. Said axial end edge is folded inwards, as described below.

The needle protection device 200 is advantageously made by molding the inner and outer bodies 210, 220, then assembling the inner body in the outer body. Preferably, the inner body is inserted in the outer body through the top opening, until the radial projection 215 of the inner body 210 comes to bear against the radial shoulder 225 of the outer body 220. The axial end edge 226 of the outer body 220 is then folded down so as to hold the inner body 210 in stationary manner in the outer body 220. Such folding down is preferably performed prior to assembling the needle protection device 200 on the injection device 100, but, alternatively, it could be performed after such assembly. The axial end edge 226 is preferably folded down while hot, typically in the range 100° C. to 200° C. as a function of the material of the outer body.

In the stored position, the needle 110 is sealed by being embedded in the dispenser orifice 111 of the needle 110 into the flexible or deformable material of the inner body 210. The injection device is advantageously sealed by contact between the axial end edge 213 of the inner body and the axial end surface 103 of the hub 102 of the syringe. Such sealing is reinforced by the inner body 210 being compressed against the axial end surface 103 of the hub 102 of the syringe, which compression is generated in particular by the position of the radial shoulder 225 and the length of the inner body 210 and/or the pressure of the outer body 220 on the inner body 210 at the folded-down axial end edge 226.

The injection device, in particular the syringe body, is advantageously sealed merely by contact between the proximal axial end edge 213 of the inner body 210 and the axial end surface 103 of the hub 102 of the syringe. In this configuration, said inner body is preferably made of rubber that presents properties that, compared to a TPE for example, are much better. Thus, rubber presents in particular the following properties: hardness that is greater than 60 on the Shore A scale, elasticity that is greater than 10 megapascal (MPa), remanent deformation on compression that is less than 25%, specific gravity that is greater than 1, in particular greater than 1.3. In addition, rubber presents only very little, if any, variations in size in the event of treatment at temperatures that are high, e.g. about 120° C. for steam sterilization. In contrast, under such circumstances, TPEs may present shrinkage, i.e. reductions in size that may be as much as 3%. For an inner body of a needle protection device, such shrinkage may signify loss of sealing in the stored position.

Figure 3:
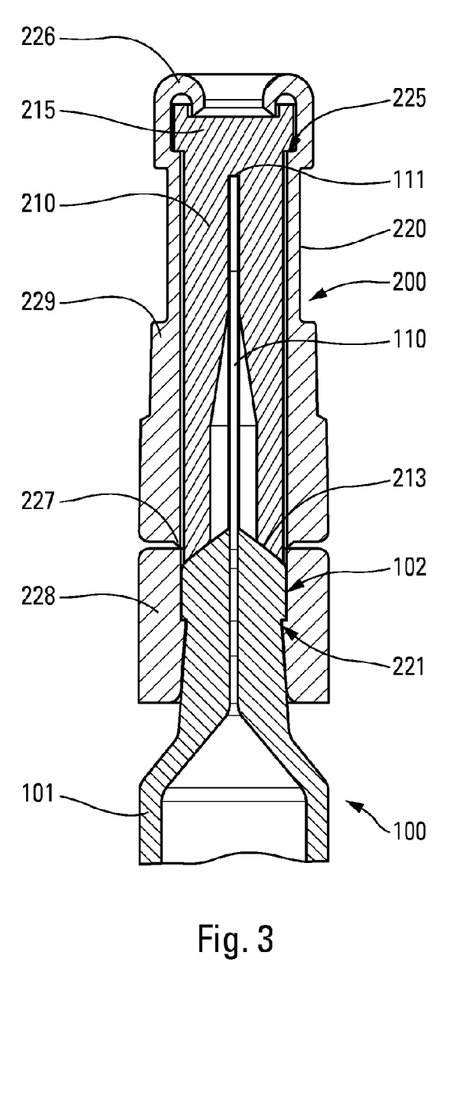
FIGS. 3 to 5 are diagrammatic section views of three other advantageous variant embodiments, in their stored positions.
Figure 4:
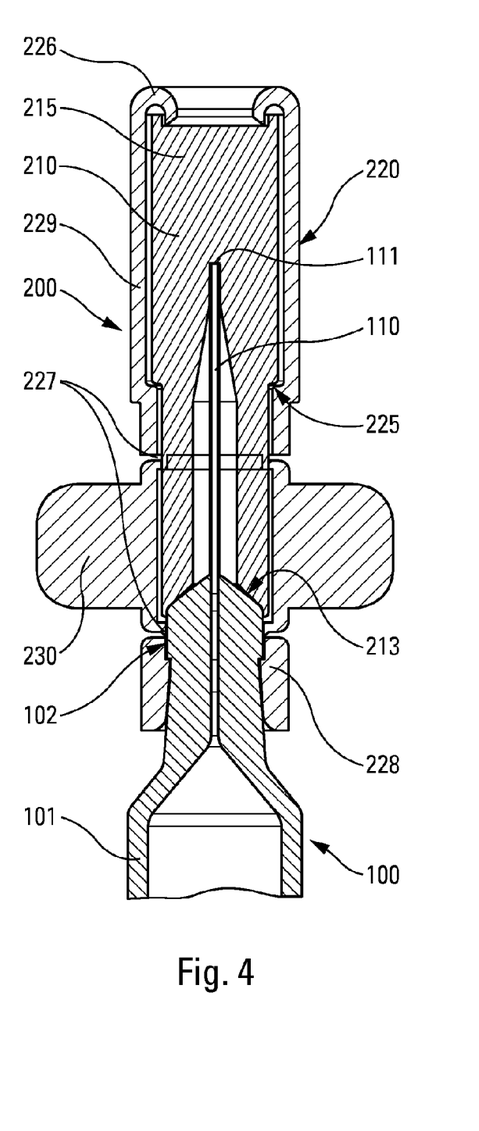
Figure 5:
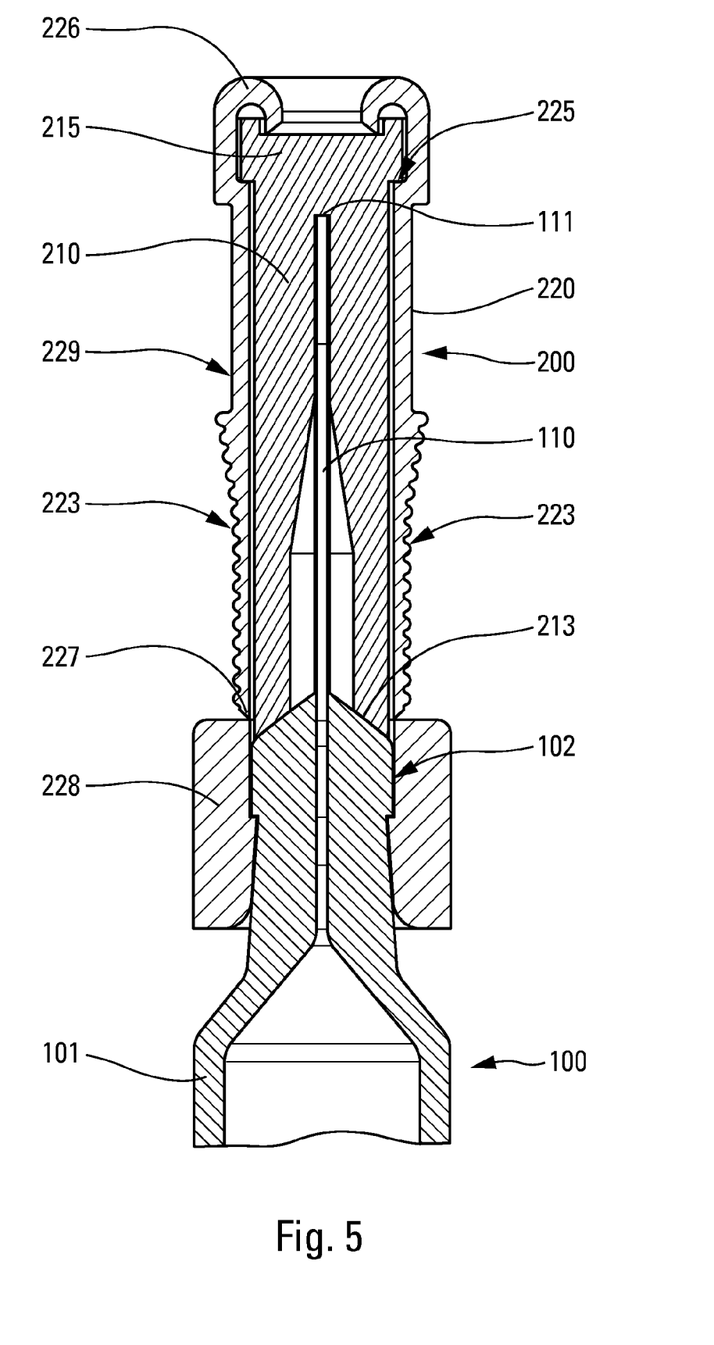
Figure 6:
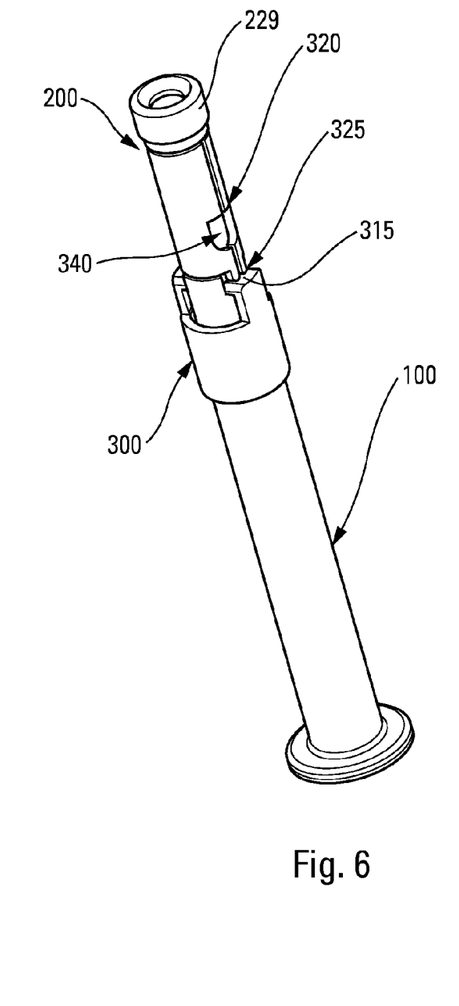
FIG. 6 is a diagrammatic perspective view of still another variant embodiment, in its stored position.
Figure 7:
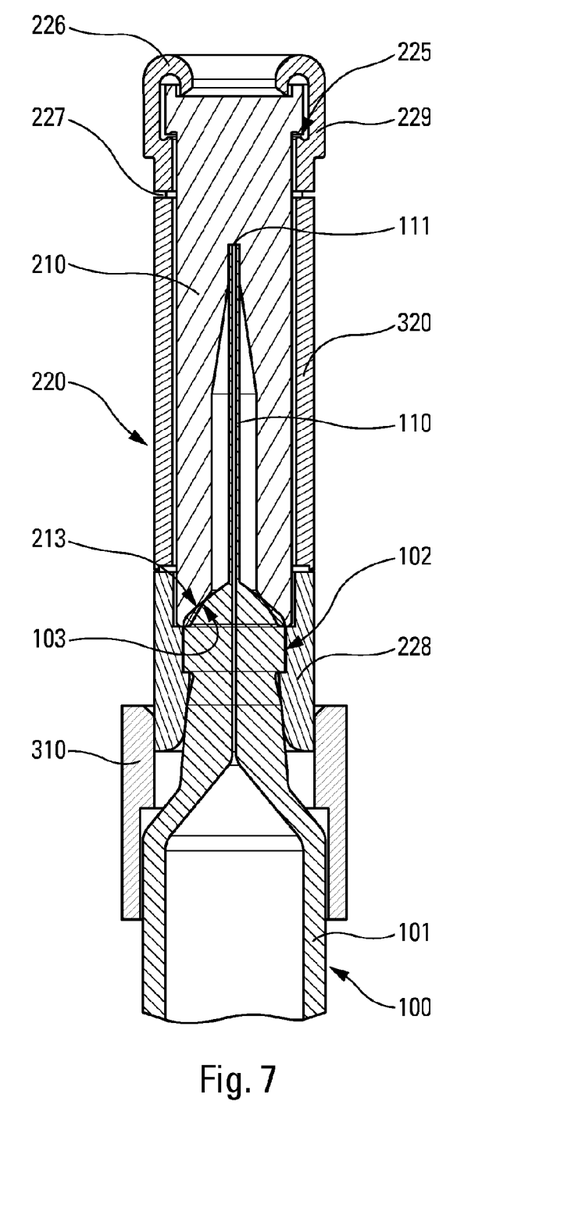
FIG. 7 is a diagrammatic section view of the FIG. 6 device.
Figure 8:
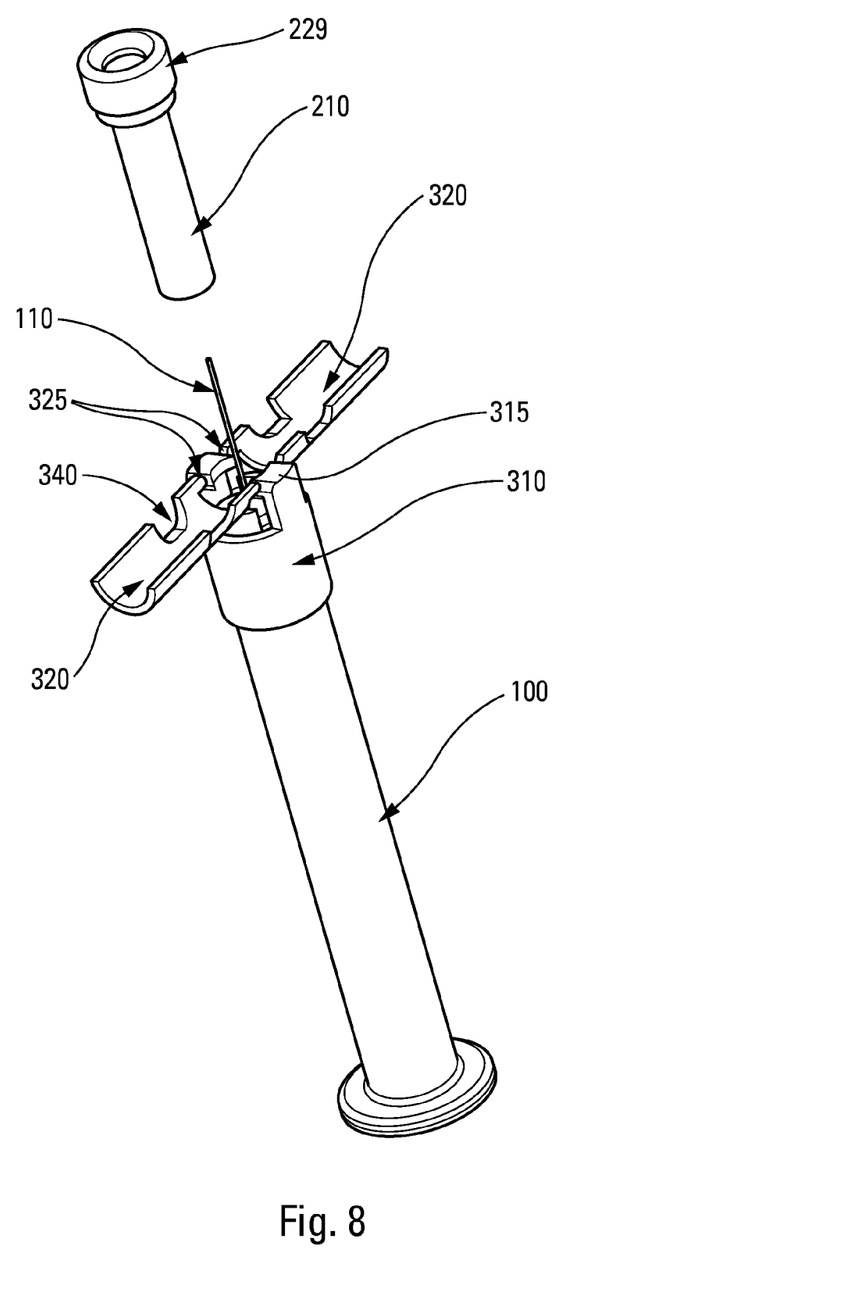
FIG. 8 is a view similar to the view in FIG. 6, but in the working position of the injection device.
Figure 9:
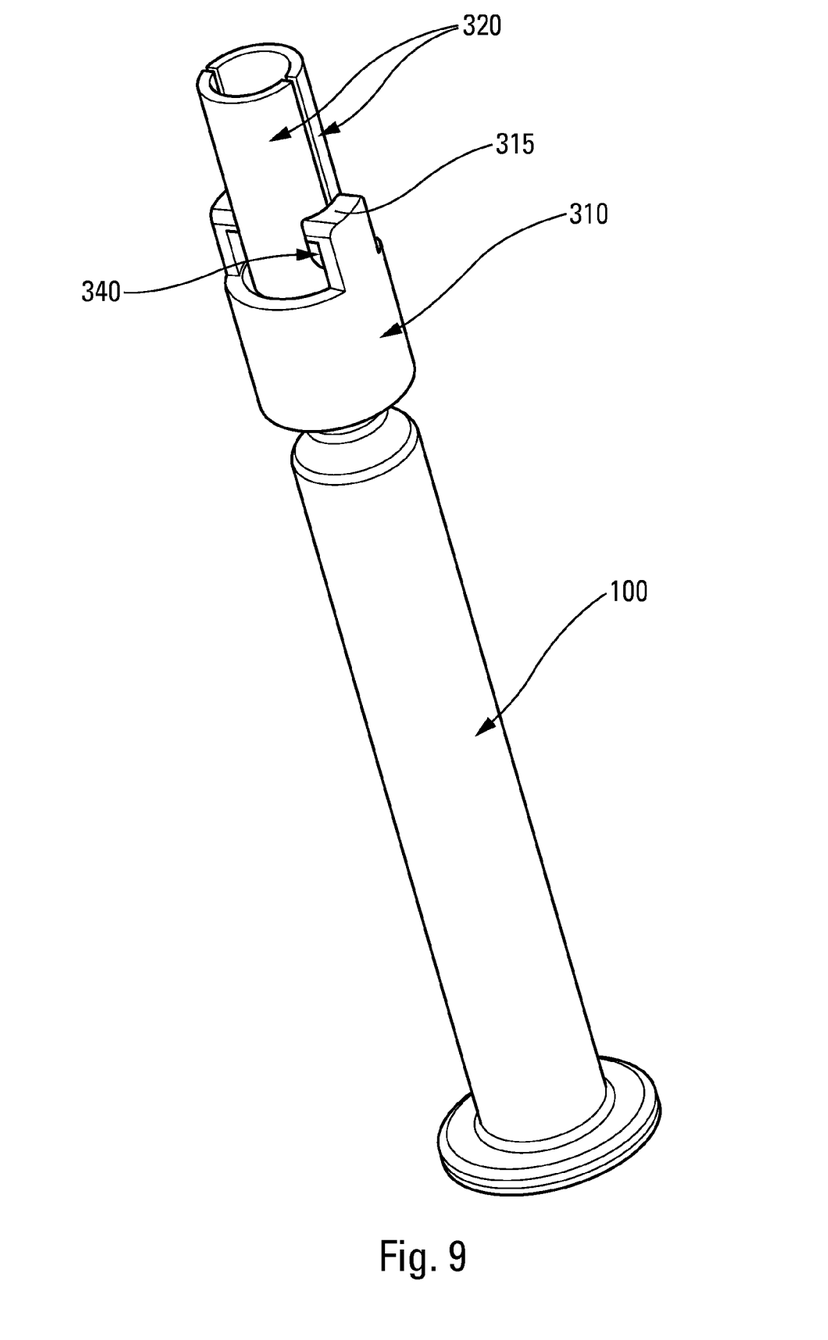
FIG. 9 is a view similar to the views in FIGS. 6 and 7, but in the end of injection position.

FIGS. 3 to 5 show advantageous variant embodiments that incorporate a first-use indicator.

In these variants, the outer body 220 includes a protective portion 229 that is connected to the fastener portion 228 via at least one breakable bridge of material 227. Thus, the outer body 220 is made as a single piece, and while the needle protection device is being removed, said at least one breakable bridge of material 227 is broken, and this forms a first-use indicator. In order to be able to remove the needle protection device, it is necessary to break the breakable bridge(s) of material, and once broken, it is no longer possible to return them to their initial state. The user who sees the bridges of material intact thus knows that the needle protection device has not been removed. However, when the bridges of material are broken, the user knows that there is a risk of loss of sealing and thus of contamination. Naturally, the force required to remove the fastener portion 228 from the injection device 100 must be greater than the force required to break the bridge(s) of material. Thus, it is guaranteed that the bridges of material always break first, and it is thus not possible to remove the needle protection device without breaking said bridges of material.

The fastener portion 228 is fastened on the injection device, in particular snap-fastened on the hub of the syringe, as described above. The protective portion 229 is fastened to said inner body 210, in particular by jamming the radial projection 215 of the inner body 210 between the radial shoulder 225 and the folded-down axial end edge 226.

FIG. 3 shows a variant embodiment in which the bridges of material 227 are broken by pulling axially on the protective portion 229. When the force is sufficient, the bridges of material 227 break, and the protective portion together with the inner body 210 may be removed from the injection device 100, while the fastener portion 228 remains fastened to the hub of the syringe.

In FIG. 4, the bridge(s) of material 227 are broken by pulling sideways on a tab 230 that is fastened firstly to said fastener portion 228 via at least one bridge of material 227, and secondly to said protective portion 229 via at least one bridge of material 227.

In FIG. 5, the protective portion 229 of the outer body 220 includes at least one manual deformation zone 223, the bridge(s) of material 227 being broken by pinching said at least one manual deformation zone 223. Advantageously, two manual deformation zones 223 are provided that are diametrically opposite each other, each of said zones 223 being connected to a bridge of material 227 that breaks when the corresponding zone is manually pinched or deformed in some other way.

FIGS. 6 to 9 show another variant embodiment in which the needle protection device 200 further includes a protection system 300 for protecting against accidental pricking, in particular after using the injection device 100.

In this variant, the protection system 300 comprises a control ring 310, preferably made of rigid plastics material like the outer body 220 of the needle protection device 200. The control ring 310 is mounted to slide over said outer body 220.

The outer body 220 is advantageously made up of two portions. A protective portion 229 that makes it possible to remove the inner body 210, and a fastener portion 228 that is fastened on the injection device 100 and that further includes protective flaps 320. The protective portion 229 is connected to the fastener portion 228, in particular to said protective flaps 320, via breakable bridges of material 227. The control ring 310 is mounted to slide around said fastener portion 228.

The control ring 310 includes at least one, and preferably two, axial end edge portions 315 that co-operate with said protective flaps 320, as described below.

The protective flaps 320 are pivotable and are connected to said fastener portion 228 via flexible hinges. They include axial tabs 325, having ends that are preferably rounded, that co-operate with said axial end edge portions 315 of the control ring 310. In their closed or covering position, the protective flaps 325 define slots 340 that can be seen in particular in FIG. 6.

In order to perform the injection, the patient or health personnel must break said bridges of material 227, remove the protective portion 229 together with the inner body 210, and slide the control ring 310 into a first position, thereby opening the protective flaps 320 and making it possible to perform the injection, the needle 110 being uncovered.

After injection, in order to reduce the risk of accidental pricking, the patient or health personnel pushes the control ring 310 into a second position, thereby causing the needle 110 to be covered by the protective flaps 320.

The needle 110 is uncovered in two steps. A first step consists in removing the inner body 210 of the needle guard, the second step resides in opening the protective flaps 320.

The inner body 210 is removed by removing the protective portion 229, which is possible after the breakable bridges of material 227 have been broken.

The protective flaps 320 are opened by sliding the control ring 310 towards the dispenser orifice 111 of the needle 110. Raising the control ring 310 in this way (in the position shown in FIGS. 6 to 9) causes said control ring 310 to thrust against the protective flaps 320, the axial end edge portions 315 of the control ring 310 pushing against the ends of the axial tabs 325 of the protective flaps 320. Such thrust causes the protective flaps 320 to pivot about their flexible hinges, thereby uncovering the needle 110.

After injection, the needle 110 is made safe by a second thrust of the control ring 310 towards the end of the needle that includes the dispenser orifice 111. The second thrust should thus be sufficient to overcome said first blocking means.

The second thrust would require the release of the axial tabs 325, enabling said control ring 310 to push the protective flaps 320 so as to close them.

The slots 340 allow the control ring 310 to pass, and in particular its axial end edge portions 315, while the needle 110 is being covered by closing the protective flaps 320.

This position with the needle uncovered is advantageously held by first blocking means, e.g. a first groove 381 of the control ring 310, that co-operate with a first rib 281 of the fastener portion 228.

This position is advantageously held by second blocking means, e.g. a second groove 382 of the control ring 310 and/or a second rib 282 of the fastener portion 228.

Figure 10:
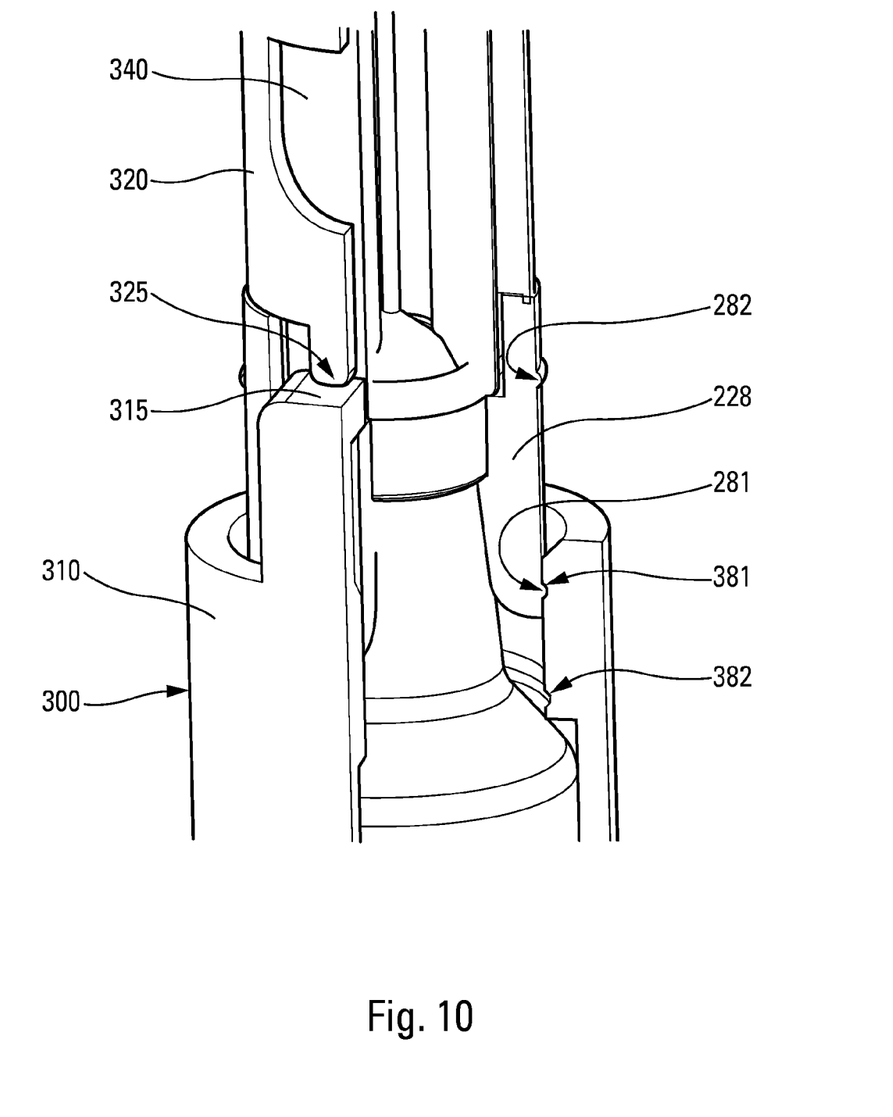
FIG. 10 is a diagrammatic and partially cut-away perspective view, showing the device in FIGS. 6 to 9.

Blocking means for blocking the control ring 310 relative to said outer body 220 are advantageously provided on said control ring and/or on said outer body, in particular its fastener portion 228. The blocking means can be made in various ways. By way of example, as shown in FIG. 10, the control ring 310 may include two grooves 381, 382 that are axially offset, and the fastener portion 228 of the outer body 220 may include two ribs 281, 282, also axially offset. Prior to actuation, the first groove 381 co-operates with the first rib 281. When the user wishes to use the device, the user pushes against the control ring 310 with a force that is sufficient to overcome the blocking means and to cause the control ring to slide over said outer body 220, so as to open the protective flaps 320, as explained above. In the open position of the flaps, the second groove 382 of the control ring co-operates with the first rib 381 of the outer body so as to hold the control ring in this working position. After injection, in order to close the flaps 320, the user should once again exert a force that is sufficient to overcome the blocking means, and to bring the control ring 310 towards the covering position of the protective flaps, in which the first groove 381 of the control ring co-operates with a second rib 282 of the outer body.

Naturally, the blocking means can be made in various ways. Thus, a single groove of the control ring may co-operate with two or three ribs of the fastener portion. In a variant, two or three grooves of the control ring could co-operate with a single rib of the fastener portion. Optionally, two ribs and two grooves could be offset in identical manner, so that in the open position of the flaps, there is a double snap-fastening of the two grooves on the two ribs.

Naturally, the blocking means could also be inverted, with one or two grooves on the fastener portion and one or two ribs on the control ring. Other embodiments are also possible.

The embodiment in FIGS. 6 to 9 combines a protection system 300 with a first-use indicator, but it is entirely possible to make the protection system 300 independently of the first-use indicator.

Naturally, the invention is not limited to the embodiments shown in the drawings, and the ambit of the invention is, on the contrary, defined by the accompanying claims.

The invention claimed is:

1. A fluid injection device comprising a syringe body and a needle that is fastened in an axial end projection of the syringe body, said axial end projection being defined between an axial end surface of the syringe body and a radial projection, said injection device further comprising a needle protection device, said protection device being fastened on said injection device in a stored position, said protection device being removable from said injection device, said protection device comprising an inner body that is made of material that is substantially flexible or deformable, and an outer body that is made of material that is substantially rigid, in the stored position said inner body closing a dispenser orifice of said needle in leaktight manner, and co-operating with said injection device in leaktight manner, and in the stored position said outer body co-operating with said injection device so as to fasten said protection device on said injection device, said outer body including a fastener portion that is fastened, in particular snap-fastened, on said radial projection of said axial end projection; wherein said needle protection device includes a protection system for protecting against accidental pricking, said protection system comprising protective flaps that form an integral part of said outer body, said protective flaps being movable between a covering position in which they cover the needle, and an open position in which the needle is uncovered, said protection system further comprising a control ring that, before injection, slides over said outer body towards the dispenser orifice of the needle so as to move said protective flaps from their covering position to their open position, and, after injection, slides over said outer body towards the dispenser orifice of the needle so as to move said protective flaps from their open position to their covering position, said control ring, while remaining attached to the fluid injection device, thereby moving with respect to the outer body and in a single axial direction towards the dispenser orifice of the needle at a free distal end of the needle, both to initially to move said protective flaps from their covering position to their open position and subsequently to move said protective flaps from their open position to their covering position.

2. A device according to claim 1, wherein said inner body includes a radial projection, and said outer body includes a radial shoulder and an axial end edge that defines a top axial opening, said inner body being inserted in said outer body through said top axial opening, with said radial projection in abutment against said radial shoulder, said axial end edge of said outer body being folded down on said inner body so as to fasten said inner body in said outer body.

3. A device according to claim 2, wherein said axial end edge of said outer body is folded down on said inner body after assembling said needle protection device on said injection device.

4. A device according to claim 2, wherein said axial end edge of said outer body is folded down on said inner body prior to assembling said needle protection device on said injection device.

5. A device according to claim 1, wherein said outer body includes a protective portion that is fastened to said inner body, said protective portion is connected to said fastener portion via at least one breakable bridge of material, said at least one breakable bridge of material being broken so as to remove said protective portion and said inner body from said injection device.

6. A device according to claim 5, wherein the force required to remove said fastener portion from said injection device is greater than the force required to break said at least one breakable bridge of material.

7. A device according to claim 1, wherein said control ring includes at least one axial end edge portion that co-operates with said protective flaps so as to move them from their covering position to their open position.

8. A device according to claim 7, wherein said protective flaps are pivotable and are connected to said outer body via flexible hinges.

9. A device according to claim 8, wherein each of said protective flaps includes at least one axial tab that co-operates with said at least one axial end edge portion of the control ring.

10. The device according to claim 9, wherein the at least one axial tab has an end that is rounded and that co-operates with the at least one axial end edge portion of the control ring.

11. A device according to claim 7, wherein, in their covering position, said protective flaps define at least one slot that is adapted to receive said at least one axial end edge portion of the control ring.

12. A device according to claim 1, wherein said outer body and/or said control ring include blocking means for holding said control ring on said outer body in a first position, with the protective flaps in their open position, and in a second position, with the protective flaps in their covering position.

13. A device according to claim 12, wherein said blocking means are formed by at least one rib that is forming on one of the outer body and the control ring, and that co-operates with at least one groove that is formed on the other one of the outer body and the control ring.

14. A device according to claim 1, wherein said inner body is made of rubber.

* * * * *